US005502152A

United States Patent [19]

Shimada et al.

[11] Patent Number: 5,502,152
[45] Date of Patent: Mar. 26, 1996

[54] CARBOXYL GROUP-CONTAINING POLYOXYALKYLENE DERIVATIVE

[75] Inventors: Shigeru Shimada, Kawasaki; Susumu Jinbo; Hideyuki Isii, both of Kanagawa, all of Japan

[73] Assignee: Hodogaya Chemical Co., Ltd., Kawasaki, Japan

[21] Appl. No.: 372,250

[22] Filed: Jan. 13, 1995

[30] Foreign Application Priority Data

Jan. 14, 1994 [JP] Japan .................. 6-014917

[51] Int. Cl.$^6$ .................................................. C08G 18/48
[52] U.S. Cl. .......................... 528/71; 252/182.27; 528/76; 528/79; 528/366; 562/468; 562/470; 562/587; 560/186
[58] Field of Search .................... 252/182.27; 562/468, 562/470, 587; 560/186; 528/71, 76, 79, 366

[56] References Cited

U.S. PATENT DOCUMENTS 5,282,987  2/1994  Balzer et al. .................... 562/587

FOREIGN PATENT DOCUMENTS 0107640  5/1984  European Pat. Off. .

*Primary Examiner*—James J. Seidleck
*Assistant Examiner*—R. F. Johnson
*Attorney, Agent, or Firm*—Oblon, Spivak, McClelland, Maier & Neustadt

[57] ABSTRACT

Disclosed is a polyoxyalkylene derivative which is useful for a carboxyl group-containing polyurethane resin, can easily introduce a carboxyl group into a polyurethane resin skeleton, and has a low melting point or is in a liquid state at normal temperature. The polyoxyalkylene derivative is represented by formula (I):

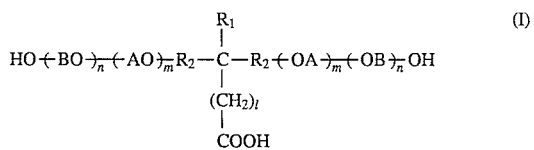

wherein $R_1$ represents a hydrogen atom or an alkyl group having from 1 to 3 carbon atoms; $R_2$ represents an alkylene group having from 1 to 6 carbon atoms or an arylene group having from 6 to 8 carbon atoms; A represents an alkylene group having from 4 to 7 carbon atoms; B represents an alkylene group having from 2 to 6 carbon atoms; l represents from 0 to 2; m represents from 0.1 to 35; n represents from 0.1 to 50; and $0.5 < (m+n) < 50$.

5 Claims, No Drawings

CARBOXYL GROUP-CONTAINING POLYOXYALKYLENE DERIVATIVE

FIELD OF THE INVENTION

The present invention relates to a polyoxyalkylene derivative having a carboxyl group and hydroxy groups useful for producing an aqueous polyurethane resin and as a modifier for various kinds of polymers, a method of producing the polyoxyalkylene derivative, and a polyurethane resin using the polyoxyalkylene derivative.

BACKGROUND OF THE INVENTION

Recently, from the view points of the dangerousness of an inflammation, an explosion, etc., the toxicity to human being, the occurrence of environmental pollution, etc., caused by organic solvents, the tendency of using aqueous resins in place of organic solvent type resins conventionally used has been increased. In particular, in regard to aqueous polyurethane resins, polymers having characteristic excellent properties are obtained by reacting many isocyanate compounds and polyol compounds each having different structures together with a chain-lengthening agent from soft elastomers to hard plastics, various investigations for obtaining aqueous polyurethane resins have been proceeded in a wide field of coating materials, adhesives, impregnants, etc.

As aqueous polyurethane resins, anion type resins, cation type resins, and nonion type resins are known but from the points of the stability with the passage of time, the physical properties thereof, the miscible stability with other emulsions or various kinds of pigments, etc., a self-emulsifying aqueous polyurethane having a carboxyl group introduced into the polyurethane resin skeleton has been watched with keen interest.

An ordinary method of introducing a carboxyl group into a polyurethane resin is practiced by reacting a polyol compound with an excessive amount of a polyisocyanate compound to synthesize an isocyanate group-terminated prepolymer and then reacting the prepolymer with a compound having at least one carboxyl group and two active hydrogen atoms capable of reacting with isocyanate groups in the molecule.

As a compound for introducing a carboxyl group into a polyurethane skeleton, the compounds described in D. Dieterich, *Progress in Organic Coatings*, 4, 281–340 (1981), etc., are known but these compounds have the problems that they all have a high melting point, the solubility thereof in polyurethane resins and organic solvents being used for polyurethane resins is poor, and the introduction of a carboxyl group into the resin skeleton is not easy.

As a compound capable of relatively easily introducing a carboxyl group into the polyurethane resin skeleton in conventionally known compounds, there is 2,2'-dimethylolpropionic acid but the compound has a high melting point and since the solubility of the compound in polyurethane resins and organic solvents is poor, it is required to use an organic solvent having a high polarity such as N-methyl-2-pyrrolidone in the case of using the foregoing compound. However, it is difficult to remove N-methyl-2-pyrrolidone, etc., which is a water-soluble high boiling solvent, from an aqueous polyurethane resin and hence there is a problem that the aqueous polyurethane resin obtained by the method is used in the state of containing the organic solvent.

SUMMARY OF THE INVENTION

The present invention has been made under these circumstances.

A first object of the present invention is to provide a polyoxyalkylene derivative which can easily introduce a carboxyl group into a polyurethane resin skeleton, etc., has a low melting point or is in a liquid state at normal temperature, and contains at least one carboxyl group and hydroxy groups in the molecule.

A second object of the present invention is to provide a method of producing the foregoing polyoxyalkylene derivative.

A third object of the present invention is to provide a carboxyl group-containing polyurethane resin particularly suitable for producing an aqueous polyurethane resin, comprising the foregoing polyoxyalkylene derivative, a polyisocyanate compound, and, if necessary, a polyol compound and a chain-lengthening agent.

As the result of various investigations for attaining the objects described above, the inventors have discovered that a novel polyoxyalkylene derivative having a carboxyl group and hydroxy groups is synthesized by addition-polymerizing a cyclic ether to the hydroxy group of a compound having a carboxylic acid alkyl ester and hydroxy groups to synthesize a polyoxyalkylene derivative having a carboxylic acid alkyl ester and hydroxy groups and then hydrolyzing the carboxylic acid alkyl ester of the polyoxyalkylene derivative, and have accomplished the present invention based on the discovery.

That is, the present invention is as follows.

1. A polyoxyalkylene derivative having a carboxyl group and hydroxy groups represented by formula (I):

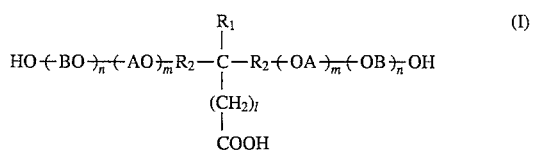

wherein $R_1$ represents a hydrogen atom or an alkyl group having from 1 to 3 carbon atoms; $R_2$ represents an alkylene group having from 1 to 6 carbon atoms or an arylene group having from 6 to 8 carbon atoms; A represents an alkylene group having from 4 to 7 carbon atoms; B represents an alkylene group having from 2 to 6 carbon atoms; l represents from 0 to 2; m represents 0.1 to 35; n represents from 0.1 to 50; and $0.5<(m+n)<50$.

2. A method of producing the foregoing polyoxyalkylene derivative having a carboxyl group and hydroxy groups by addition-polymerizing a 5-membered cyclic ether and a 3- or 4-membered cyclic ether to a compound having a carboxylic acid alkyl ester group and hydroxy groups represented by formula (II) using a Lewis acid to synthesize a polyoxyalkylene derivative having a carboxylic acid alkyl ester group and hydroxy groups, and then hydrolyzing the polyoxyalkylene derivative in the presence of a base or an acid:

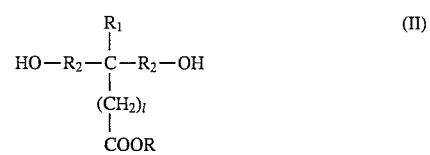

wherein R represents an alkyl group having from 1 to 8 carbon atoms; $R_1$ represents a hydrogen atom or an alkyl group having from 1 to 3 carbon atoms; $R_2$ represents an alkylene group having from 1 to 6 carbon atoms or an arylene group having from 6 to 8 carbon atoms; and l represents an integer of from 0 to 2.

3. A carboxyl group-containing polyurethane resin comprising the foregoing polyoxyalkylene derivative having a carboxyl group and hydroxy groups, a polyisocyanate compound, and, if necessary, a polyol compound and a chain-lengthening agent.

DETAILED DESCRIPTION OF THE INVENTION

Then, the present invention is described in detail.

The polyoxyalkylene derivative represented by formula (I) is a mixture of the compounds which are different in the number of the —(AO)— moiety and the number of the —(BO)— moiety. The numerals m and n in formula (I) mean an average of the number of —(AO)— and an average of the number of —(BO)—, respectively. The numerals m and n are calculated using the average molecular weight obtained by gel permeation chromatography and the information of NMR analysis.

$R_1$ preferably represents $CH_3$—, $R_2$ preferably represents —$CH_2$—, A preferably represents —$CH_2CH_2CH_2CH_2$— o

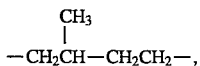

B preferably represent

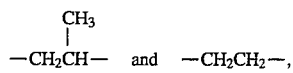

l preferably represents zero, m preferably represents 1 to 15, and n preferably represents 0.5 to 5.

The compound having a carboxylic acid alkyl ester and hydroxy groups being used in the present invention is the compound shown by following formula (II):

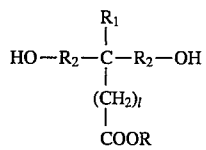

wherein R represents an alkyl group having from 1 to 8 carbon atoms; $R_1$ represents a hydrogen atom or an alkyl group having from 1 to 3 carbon atoms; $R_2$ represents an alkylene group having from 1 to 6 carbon atoms or an arylene group having from 6 to 8 carbon atoms; and l represents an integer of from 0 to 2.

As specific examples of the compound represented by formula (II), there are the alkyl esters having from 1 to 8 carbon atoms of a compound having one carboxyl group and two hydroxy groups, such as 2,2-bis(hydroxymethyl)propionic acid, 4,4-bis(4-hydroxyphenyl)valeric acid, bis(4-hydroxyphenyl)acetic acid, etc.

As the Lewis acid being used in the present invention, there are metal halides or non-metal halides, such as boron trifluoride, phosphorus pentafluoride, antimony pentafluoride, antimony pentachloride, aluminum chloride, ferric chloride, titanium tetrachloride, tin tetrachloride, lithium hexafluorophosphate, etc.; solid acids such as silicon dioxide, titanium dioxide, zirconium dioxide, aluminum oxide, etc., the solid acids obtained by adding the foregoing halides to the foregoing solid acids; and complexes of boron trifluoride, antimony pentafluoride, etc., and a chain or cyclic ether such as dimethyl ether, diethyl ether, tetrahydrofuran (THF), etc. Among them, a complex of boron trifluoride and THF is particularly preferred.

As the 3- or 4-membered cyclic ether compound being used in the present invention, there are 3-membered cyclic alkylene oxides such as ethylene oxide, 1,2-propylene oxide, 1,2-butylene oxide, 2,3-butylene oxide, epichlorohydrin, etc., and 4-membered cyclic alkylene oxides such as 1,3-propylene oxide, 1,3-butylene oxide, 2-methyl-1,3-epoxypropane, 2,2-dimethyl-1,3-epoxypropane, etc. Among them, ethylene oxide and propylene oxide are particularly preferred.

These Lewis acids can be used singly or as a mixture thereof.

As the 5-membered cyclic ether compound being used in the present invention, there are tetrahydrofuran, 3-methyltetrahydrofuran, 3-ethyltetrahydrofuran, 2-methyltetrahydrofuran, etc.

In the case of practicing the present invention, the kinds and the amounts of the compound having a carboxylic acid alkyl ester group and hydroxy groups, the cyclic ether compound, and the catalyst to be used must be selected according to the molecular structure and the molecular weight of the desired polyoxyalkylene derivative.

In the case of addition polymerizing a 5-membered cyclic ether to the hydroxy group, since the addition polymerization does not proceed using a Lewis acid alone, the addition polymerization is practiced by adding a 5-membered cyclic ether to the compound having a carboxylic acid alkyl ester group and hydroxy groups to dissolve the compound, then adding a Lewis acid to the solution, and gradually adding dropwise a 3- or 4-membered cyclic ether to the mixed solution to carry out the reaction. As to the amount ratio of each component to the hydroxy group of the compound of formula (II), the amount of the Lewis acid is generally from 0.01 to 2 moles, preferably from 0.04 to 0.5 moles, and the amount of the 3- or 4-membered cyclic ether is generally from 0.5 to 50 moles and preferably from 1 to 10 moles, per mole of the hydroxyl group. The amount of the 5-membered cyclic ether is determined by the relation with the amount of the 3- or 4-membered cyclic ether, but is usually used in an excessive amount since the 5-membered cyclic ether serves as a solvent, and the unreacted ether is recovered after the polymerization reaction for reuse.

When it is necessary to improve the solubility of the product, an inert organic solvent such as toluene, xylene, diethyl ether, dibutyl ether, etc., may be used.

The reaction is carried out generally at a temperature of from −20° C. to 60° C., and preferably from 0° C. to 40° C. It is preferred that the reaction is carried out under a substantially water free condition, e.g., under a dry nitrogen gas stream. The reaction is generally conducted from 1 to 15 hours in the foregoing temperature range and then from 2 to 6 hours at a temperature range of from 0° C. to 10° C.

The polymerization finished liquid is neutralized with an aqueous solution of an alkali such as sodium hydroxide, potassium hydroxide, sodium hydrogencarbonate, etc., and after removing the unreacted cyclic ether by distillation, etc., the aqueous layer containing the catalyst decomposition products is separated. When the neutralization of the solid acid, etc., is unnecessary, after separating the catalyst component by subjecting the polymerization finished liquid to an adsorption filtration as it is, the unreacted cyclic ether is recovered. The organic layer containing a polymer produced is purified by a known method such as water washing, an adsorption, a filtration, etc., to provide the polyoxyalkylene derivative having a carboxylic acid alkyl ester group and hydroxy groups.

The polyoxyalkylene derivative having a carboxyl group and hydroxy groups of the present invention is obtained by adding an aqueous solution of an alkali such as sodium hydroxide, potassium hydroxide, etc., to the polyoxyalkylene derivative having a carboxylic acid alkyl ester group and hydroxy groups obtained by the method described above and carrying out the hydrolysis reaction (saponification reaction). The hydrolysis reaction is efficiently carried out at a temperature of from 60° C. to 100° C., using an alkali at least in the equimolar amount to the carboxylic acid alkyl ester group, and if necessary, adding a water-soluble solvent such as a lower alcohol (e.g., ethanol) and THF. The hydrolysis reaction can be also practiced in the presence of an acid catalyst such as hydrochloric acid, sulfuric acid, a solid acid, etc.

There is no particular restriction on the polyisocyanate compound being used in the present invention and there are aliphatic, aromatic, and cyclic diisocyanate compounds such as tolylene diisocyante, 4,4'-diphenylmethane diisocyanate, 3,3'-dimethyldiphenylmethane-4,4'-diisocyanate, p-phenylene diisocyanate, 1,5-naphthalene diisocyanate, m-xylene diisocyanate, tetramethylxylene diisocyanate, 1,6-hexamethylene diisocyanate, 1,4-tetramethylene diisocyanate, trimethylhexamethylene diisocyanate, 1,3-bisiisocyanate methylcyclohexane, 4,4'-dicyclohexylmethane diisocyanate, 1,4-bisisocyanate methylcyclohexane, etc.

Any conventionally known polyol may be used in combination with the polyoxyalkylene derivative of formula (I) for the production of the polyurethane resin according to the present invention, and the examples thereof include polyether polyols such as polyoxypropylene polyol, polyoxytetramethylene glycol, etc.; polyester polyols such as polybutylene adipate polyol, polyhexamethylene adipate polyol, polycaprolactone polyol, polyhexamethylene carbonate, etc.

As the chain-lengthening agent being used in the present invention, there are glycols such as ethylene glycol, butanediol, etc.; diamine compounds such as ethylenediamine, isophoronediamine, hydrazine, etc.

The production of the aqueous polyurethane resin using the polyoxyalkylene derivative having a carboxyl group and hydroxy groups of the present invention is described below.

That is, by reacting a conventionally known polyol and an excessive amount of a polyisocyanate compound in the presence or absence of a solvent, an isocyanate group-terminated prepolymer is synthesized and then by reacting the prepolymer and the polyoxyalkylene derivative having a carboxyl group and hydroxy groups of the present invention, an isocyanate group-terminated prepolymer having a carboxyl group is synthesized. Then, the aqueous polyurethane resin of the present invention is synthesized by mechanically dispersing and emulsifying the prepolymer in deionized water containing an inorganic base such as sodium hydroxide, etc., or an organic base such as triethylamine, tributylamine, dimethylethanolamine, morpholine, etc., and, if necessary, a chain-lengthening agent such as ethylenediamine, isophoronediamine, etc.

In other method, the aqueous polyurethane resin can be also synthesized by polymerizing the isocyanate group-terminated prepolymer having a carboxyl group with the foregoing chain-lengthening agent such as ethylenediamine, etc., and after making the carboxyl group of the polymer to a salt thereof with an organic base such as triethylamine, etc., and mechanically dispersing and emulsifying the polymer in deionized water.

In the preparation of the aqueous polyurethane resin, the polyoxyalkylene derivative of formula (I), the other polyols, the polyisocyanate compound, and a chain-lengthening agent are generally added in an equivalent ratio of from 0.02 to 0.50, from 0 to 0.50, from 0.50 to 0.67, and from 0 to 0.50, respectively.

The polyoxyalkylene derivative having a carboxyl group and hydroxy groups of the present invention is in a liquid state at normal temperature or has a low melting point and since the polyoxyalkylene derivative can be reacted with the isocyanate group-terminated prepolymer without using solvent, in addition to the foregoing aqueous polyurethane resin, carboxyl group-containing polyurethane resins can be easily produced using the polyoxyalkylene derivative having a carboxyl group and hydroxy groups of the present invention by the methods of producing conventionally known polyurethane resins, and the polyurethane resins can be used as solvent-type adhesives and solventless-type thermoplastic urethane ionomers.

Then, the following examples are intended to illustrate the present invention practically but not to limit the invention in any way. In addition, all parts and percentages in these examples, unless otherwise indicated, are by weight.

In these examples, the hydroxyl value is the value measured by a pyridine-acetic anhydride method. The gel permeation chromatography (GPC) was practiced using a high-speed chromatography (manufactured by TOSOH CORPORATION) under the conditions of using TSK-G2500HX/G4000HX as the column and tetrahydrofuran as the solvent. The number average molecular weight by GPC was calculated by the calibration curve obtained by a commercially available polyethylene glycol standard reagent. Also, the 1H-NMR analysis and the 13C-NMR analysis were carried out by GSX-400 and FT-HNR (manufactured by JEOL Ltd.).

EXAMPLE 1

In a four neck 500 ml flask equipped with a stirrer, a thermometer, and a silica gel tube, the inside atmosphere of which was replaced with a nitrogen gas, were placed 57 parts of 2,2-dimethylolpropionic acid n-butyl ester and 144.2 parts of tetrahydrofuran. The mixture was stirred under cooling by an ice-cooling bath, 7.0 parts of boron trifluoride tetrahydrofuran complex was added thereto, and then 58.1 parts of propylene oxide was gradually added to the mixture by a dropping funnel over a period of 2 hours at a temperature of from 5° C. to 10° C. Thereafter, after carrying out the polymerization reaction for 4 hours at a temperature of from 5° to 10° C., 320 parts of an aqueous solution of 10% sodium carbonate was added to the reaction system to stop the polymerization.

Then, a distillation apparatus was set to the flask and unreacted tetrahydrofuran was distilled off by heating. After allowing to cool and stand the reaction mixture to form an upper organic layer and a lower aqueous layer, the lower aqueous layer was removed. Then, 200 parts of toluene and 100 parts of water were added to the organic layer and after raising the temperature thereof to 60° C., the mixture was stirred to wash the organic layer, and then allowed to cool and stand to form an upper organic layer and a lower aqueous layer, and the lower aqueous layer was removed. Further, water washing was conducted by adding 150 parts of water to the remaining organic layer and stirring the mixture at 60° C., allowed to stand to form an upper organic layer and a lower aqueous layer, and removing the lower aqueous layer, and the same water washing was repeated further three times. Then, toluene was distilled off from the organic layer under reduced pressure at 100° C. to provide 199 parts of a colorless transparent polymer which was in a liquid state at normal temperature.

The hydroxyl value (mgKOH/g) of the polymer was 151, the acid value thereof was 0.8, and the results of the GPC analysis and the NMR analysis showed that the 2,2-dimethylolpropionic acid n-butyl ester used as the raw material had been vanished and the polymer obtained was a tetrahydrofuran-propylene oxide-added copolymerized polyol having an average molecular weight of 738.

EXAMPLE 2

In a one liter four neck flask equipped with a stirrer, a thermometer, and a condenser were placed 150 parts of the copolymerized polyol synthesized in Example 1, 150 parts of toluene, 50 parts of tetrahydrofuran, and 200 parts of an aqueous solution of 30% sodium hydroxide and the hydrolysis was carried out with a hot water bath of 80° C. for 3 hours. After allowing to cool, the reaction mixture was neutralized using 4N hydrochloric acid, and after allowing to cool and allowing to stand the mixture to form an upper organic layer and a lower aqueous layer, the lower aqueous layer was removed. Further, water washing was conducted by adding 100 parts of water to the remaining organic layer and stirring the mixture at 60° C. for 20 minutes, allowed to stand to form an upper organic layer and a lower aqueous layer, and removing the lower aqueous layer, and the same water washing was repeated further three times. Toluene and tetrahydrofuran were removed under reduced pressure from the resulting organic layer to provide 121.5 parts of a transparent polymer which was in a liquid state having a viscosity of 1260 cps/22° C. at normal temperature.

The acid value of the polymer was 69, the hydroxyl value thereof was 137, and the average molecular weight by the GPC analysis was 817. Also, the result of the NMR analysis showed that the polymer had added thereto 3.1 moles of tetrahydrofuran and 2.1 moles of propylene oxide per one equivalent of the hydroxyl group of 2,2-dimethylolpropionic acid. The resulting polymer is a compound represented by formula (I) where $R_1=CH_3-$, $R_2=-CH_2-$, $A=-CH_2CH_2CH_2CH_2-$

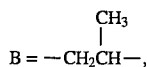

m=3.1 and n=2.1.

EXAMPLE 3

In a 500 ml four neck flask equipped with a stirrer, a thermometer, and a silica gel tube were placed 152.1 parts of polyhexamethylene carbonate diol having a hydroxyl value of 54.2 (N-960R, trade name, made by Nippon Polyurethane Industry Co., Ltd.) and 28.7 parts of hexamethylene diisocyanate (HDI, trade name, made by Nippon Polyurethane Industry Co., Ltd.), after carrying out the reaction for 5 hours at 85° C. under a nitrogen gas stream, 39.9 parts of the polyoxyalkylene derivative having an acid value of 69 and a hydroxyl value of 137 synthesized in Example 2 was added to the mixture, and the reaction was carried out for 5 hours at 85° C. to provide an isocyanate group-terminated prepolymer having a carboxyl group.

Then, to the prepolymer were added 4.9 parts of an acetone solution containing 10% by weight hydrazine monohydrate and 150 parts of acetone and after carrying out the reaction for one hour at 40° C., 5.9 parts of triethylamine was added to the reaction mixture followed by stirring for 10 minutes at 40° C. to form the salt. Then, 360 parts of the prepolyer was forcibly emulsified in 250 parts of water under stirring in a homo-mixer. After distilling off acetone in the polyurethane emulsion obtained under heat and reduced pressure, the polyurethane emulsion aged for 5 days.

The polyurethane emulsion obtained was an emulsion having 36.5% by weight solid components, a viscosity of 3800 cps/20° C., and pH 7.5 and showing a good mechanical stability.

A film of about 200 μm in thickness was formed using the polyurethane emulsion at room temperature and heat-treated at 80° C. for 30 minutes. The tensile properties of the film were measured under two conditions, 1) at a normal state (20° C., 65% RH) and 2) after water immersion (the measurement was conducted by immersing the film in water (20° C., 24 hours), taking it out, and immediately the measurement was conducted at 20° C.). The obtained results are shown in Table below.

The tensile properties were measured using Tensilon UTM-III-100 (trade name, manufactured by Orienteck K.K.) at a tensile speed 500 mm/minute.

TABLE

| Measured Condition | Tensile Properties | | | |
| --- | --- | --- | --- | --- |
|  | 100% Modulus (kgf/cm²) | 300% Modulus (kgf/cm²) | Tensile Strength (kgf/cm²) | Elongation (%) |
| Normal State | 19 | 44 | 311 | 800 |
| Water Immersion | 20 | 64 | 305 | 680 |

COMPARATIVE EXAMPLE 1

The same reaction as in Example 3 was carried out except that 2,2-dimethylolpropionic acid was used in place of the polyoxyalkylene derivative of the present invention, and 152.1 parts of polyhexamethylene carbonate, 26.8 parts of hexamethylene diisocyanate, and 5.5 parts of dimethylolpropionic acid were used such that the ratio of idocyanate group/hydroxy group of the raw materials constituting the polyurethane resin and the carboxylic acid content in the polyurethane resin were same as those in Example 3. As the result thereof, a part of dimethylolpropionic acid was dissolved but the greater part thereof was not dissolved.

When the prepolymer obtained was forcibly emulsified in water using a homo-mixer, a good polyurethane emulsion was not obtained.

The polyoxyalkylene derivative of the present invention is an oligomer having a carboxyl group and hydroxy groups as different functional groups and has a low melting point or is in a liquid state at normal temperature, and the polyoxyalkylene derivative can be used as a hydrophilic property imparting agent and a modifier for polymers.

The carboxyl group-containing polyurethane of the present invention can be suitable used for producing, in particular, an aqueous polyurethane resin and the aqueous polyurethane resin has an excellent stability and excellent mechanical properties and can be used as coating materials, adhesives, binders, etc.

While the invention has been described in detail with reference to specific embodiments, it will be apparent to one skilled in the art that various changes and modifications can be made to the invention without departing from its spirit and scope.

What is claimed is:

1. A polyoxyalkylene containing compound having a carboxyl group and hydroxy groups represented by formula (I):

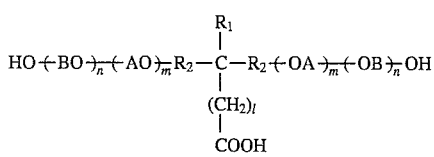

wherein $R_1$ represents a hydrogen atom or an alkyl group having from 1 to 3 carbon atoms; $R_2$ represents an alkylene group having from 1 to 6 carbon atoms or an arylene group having from 6 to 8 carbon atoms; A represents an alkylene group having from 4 to 7 carbon atoms; B represents an alkylene group having from 2 to 6 carbon atoms; l represents from 0 to 2; m represents from 0.1 to 35; n represents from 0.1 to 50; and $0.5<(m+n)<50$.

2. A method of producing a polyoxyalkylene containing compound having a carboxyl group and hydroxy groups represented by formula (I):

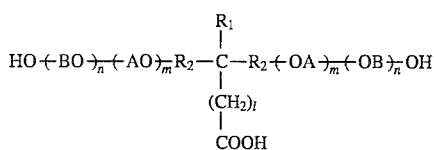

wherein $R_1$ represents a hydrogen atom or an alkyl group having from 1 to 3 carbon atoms; $R_2$ represents an alkylene group having from 1 to 6 carbon atoms or an arylene group having from 6 to 8 carbon atoms; A represents an alkylene group having from 4 to 7 carbon atoms; B represents an alkylene group having from 2 to 6 carbon atoms; l represents from 0 to 2; m represents from 0.1 to 35; n represents from 0.1 to 50; and $0.5<(m+n)<50$;

which comprises addition-polymerizing a 5-membered cyclic ether and a 3- or 4-membered cyclic ether to a compound having a carboxylic acid alkyl ester group and hydroxy groups represented by formula (II);

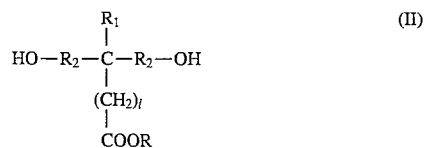

wherein R represents an alkyl group having from 1 to 8 carbon atoms; $R_1$ represents a hydrogen atom or an alkyl group having from 1 to 3 carbon atoms; $R_2$ represents an alkylene group having from 1 to 6 carbon atoms or an arylene group having from 6 to 8 carbon atoms; and l represents an integer of from 0 to 2;

using a Lewis acid to synthesize a polyoxyalkylene containing compound having a carboxylic acid alkyl ester group and hydroxy groups; and hydrolyzing the polyoxyalkylene containing compound in the presence of a base or an acid.

3. The method of claim 2, wherein the addition-polymerization is conducted at a temperature of $-20°$ C. to $60°$ C. for 1 to 15 hours and then at a temperature of $0°$ to $10°$ C. for 2 to 6 hours.

4. A carboxyl group-containing polyurethane resin comprising a polyoxyalkylene containing compound having a carboxyl group and hydroxy groups represented by formula (I) and a polyisocyanate compound:

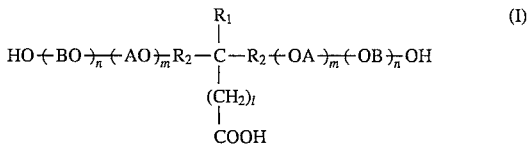

wherein $R_1$ represents a hydrogen atom or an alkyl group having from 1 to 3 carbon atoms; $R_2$ represents an alkylene group having from 1 to 6 carbon atoms or an arylene group having from 6 to 8 carbon atoms; A represents an alkylene group having from 4 to 7 carbon atoms; B represents an alkylene group having from 2 to 6 carbon atoms; l represents from 0 to 2; m represents from 0.1 to 35; n represents from 0.1 to 50; and $0.5<(m+n)<50$.

5. The carboxyl group-containing polyurethane resin of claim 4, which further comprises at least either of other polyol compound than the polyoxyalkylene containing compound of formula (I) and a chain-lengthening agent.

* * * * *